United States Patent [19]

Mariette et al.

[11] Patent Number: 5,763,732
[45] Date of Patent: Jun. 9, 1998

[54] METHOD OF ISOMERIZING N-PARAFFINS INTO ISOPARAFFINS

[75] Inventors: Laurent Mariette, Deauville; Marc Fersing, Sainte Adresse; Michel Laborde; Jacques Couillard, both of Le Havre, all of France

[73] Assignee: Total Raffinage Distribution, S.A., Puteaux, France

[21] Appl. No.: 385,447

[22] Filed: Feb. 8, 1995

[30] Foreign Application Priority Data

Feb. 8, 1994 [FR] France ............... 94 01400

[51] Int. Cl.$^6$ .................. C07C 5/13; B01J 21/20; B01J 27/13
[52] U.S. Cl. .................. 585/748; 585/747; 585/734; 502/20; 502/227
[58] Field of Search .................. 585/734, 750, 585/741, 747, 748; 502/227, 20, 228; 208/155

[56] References Cited

U.S. PATENT DOCUMENTS

| | | | |
|---|---|---|---|
| 3,440,300 | 4/1969 | Estes et al. | 260/638.68 |
| 3,791,960 | 2/1974 | Davies et al. | 208/57 |
| 4,049,739 | 9/1977 | Zabransky et al. | 260/671 R |
| 5,523,503 | 6/1996 | Funk et al. | 585/446 |

FOREIGN PATENT DOCUMENTS 1546658  11/1968  France.

Primary Examiner—Glenn Caldarola
Assistant Examiner—Alexander G. Ghyka
Attorney, Agent, or Firm—Frommer Lawrence & Haug LLP; A. Thomas S. Safford

[57] ABSTRACT

A method of isomerizing n-paraffins into isoparaffins in a cut of hydrocarbons with four carbon atoms or of hydrocarbons with five and/or six carbon atoms. The cut being processed enters at least one reactor containing a stationary catalyst bed. The charge travels over the bed. Either the rate of isomerization in the effluents or a parameter directly dependent thereon (such as the octane number) is preferably continuously measured. Some of the upstream catalyst, specifically between ⅓ and ⅔, is replaced with fresh catalyst once that rate has decreased 10 to 30% below a prescribed point. The charge is redirected through the reactor once the catalyst has been replaced.

20 Claims, 4 Drawing Sheets

METHOD OF ISOMERIZING N-PARAFFINS INTO ISOPARAFFINS

RELATED APPLICATION

This application claims priority to French Application No. 94.01400, filed Feb. 8, 1994, incorporated herein by reference.

FIELD OF THE INVENTION

The present invention relates to a method of isomerizing n-paraffins into isoparaffins.

BACKGROUND OF THE INVENTION

Among the catalysts that can be employed in known procedures for isomerization are platinum and optionally another metal from the group zirconium, titanium, molybdenum, and tungsten on a support containing a zeolite (see U.S. Pat. No. 4,830,998 and European counterpart Patent EP A 0 253 743, hereby incorporated herein by reference). Such catalysts are called "zeolitic", and they lead to relatively high temperatures of reaction.

Catalysts called "amorphous" are often preferred because they allow isomerization at much lower temperatures (between 100°–200° C.), and isomers can be obtained at close to thermodynamic equilibrium. An amorphous catalyst usually has a solid and stable support consisting of aluminum, platinum, and optionally at least one of the metals tin, nickel, germanium, rhenium, lead or of the metals from groups IB, I'B, VB, VIIB, III, and IV of the periodic table. Such metals also have Lewis sites of the metal-halogen type and Brönstedt sites (see U.S. Pat. No. 5,151,400 and French counterpart Patent FR-A 2 649 989, hereby incorporated herein by reference).

However, amorphous catalysts also have major drawbacks. They are expensive and take a long time to produce. They can be inactivated by various substances such as oxygen, water, hydrogen sulfide, olefins, aromatic hydrocarbons, etc. Lewis sites and Brönstedt sites in particular are destroyed by water, generating hydrochloric acid, and the catalyst cannot in this event be regenerated. Finally, significant quantities (usually from 5 to more often 50 metric tons) are difficult to monitor and control, considering their aggressive nature.

U.S. Pat. No. 3,791,960 (hereby incorporated herein by reference) describes a method of isomerizing paraffinic hydrocarbons at a boiling point within the range of that of the gasolines which employs a catalyst that comprises a platinum metal, a support in the form of a refractory oxide, and chlorine at active isomerization sites. The charge, which includes a minimal portion of aromatic components, initially travels through a hydrogenation section accommodating the catalyst and operating at a temperature of 150° to 350° C. in a hydrogen-rich recirculated gas containing hydrogen chloride for the purpose of hydrogenating the aromatic compounds. The effluent from the hydrogenation section is then cooled and processed in an isomerization section at 100° to 204° C. while a compound that tends to produce hydrogen chloride is introduced into the system between the hydrogenation section and the isomerization section. The effluent from the isomerization section is processed to separate the hydrogen-rich recirculated gas that contains hydrogen chloride, and returns it to the hydrogenation section.

To determine the extent of conversion into branched-chain compounds, the rate of isomerization is defined. It can be measured by chromatography of the reactor effluents or by other analytic means available to one of skill in the art such as infrared radiation, mass spectroscopy, or nuclear magnetic resonance.

A single reactor is generally used to isomerize $C_4$ cuts, which include fewer compounds that might poison the catalyst than $C_5$–$C_6$ cuts do, and the rate of isomerization is:

$$\frac{\text{isobutane}}{\text{n-butane} + \text{isobutane}}$$

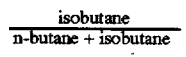

The isomerization rate employed for the $C_5$ and $C_6$ cuts to increase the charge's octane index is:

$$\frac{\text{isopentane}}{\text{pentane}} + \frac{\text{2,2-dimethylbutane}}{\text{hexane}},$$

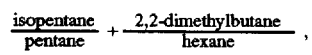

and it is also possible to detect conversion into branched-chain compounds from the octane number as determined by chromatography. When adding an appropriate new catalyst to the reactors, these isomerizing methods make it possible to increase the octane number of a paraffinic $C_5$–$C_6$, cut from approximately 60 to approximately 80 at the exit from the first reactor and approximately 81 at the exit from the second reactor.

In the refinery, it is naturally important to maintain the rate of isomerization for the $C_4$ hydrocarbons and either the octane number or the isomerization rate for the $C_5$–$C_6$ cuts as high as possible in the effluents, in that each decrease in that index translates into an economic loss. It is possible to establish a correlation between the isomerization rate and octane number, given that the isomerization rate varies from 0.1 to 30% and the octane number from 0.01 to 3%.

In the operation of refinery reactors, it is impossible to verify the state of the catalyst on site because of the large amount of catalyst used (approximately 10 to more than 50 metric tons) and because of the large size of the reactor (several meters in diameter). Furthermore, the environment is corrosive and aggressive, and the risk of deactivating the catalyst by opening the reactor is not insignificant. All that can be done is to continuously monitor the isomerization rate of the charge being processed, or a parameter directly related to that rate, the octane number for example, in the effluents. Once that parameter decreases considerably, the exploitation losses attached to the diminution of significant amounts of isomer will obviously necessitate replacing the used catalyst, no matter what its state, with fresh catalyst.

The reactor can be emptied without special precautions since the catalyst cannot be used again.

A series of two isomerization reactors is often employed for the maximum exploitation of a catalyst that cannot be regenerated, especially when a lot of isomer is needed, as is usually the case in Europe for high-octane gasolines. The catalyst in the downstream reactor usually compensates to some extent for the decreased isomerization of the effluents from the upstream reactor.

However, when the upstream reactor is deactivated for any length of time the refinery operator is faced with a choice between the lesser of two evils. On the one hand, the demand for isomer may be high enough to justify replacement of the upstream catalyst as a precaution, no matter how active it still may be, as soon as the level of isomer in the effluents begins to decrease.

On the other hand, the isomerization in the upstream reactor can be pushed until the catalyst is totally inactive, which entails exploitation losses due to the decreased activity of the catalyst in the downstream reactor, expressed as a decrease in the isomerization rate at that point.

3

Therefore, it would be advantageous to design a method of isomerizing n-paraffins into isoparaffins that consumes less catalyst while maintaining the rate of isomerization of the effluents at a maximum.

OBJECTS AND SUMMARY OF THE INVENTION

The present invention eliminates the drawbacks of the prior art by the surprisingly novel combination of one or two reactors using an amorphous catalyst with Lewis sites of the metal-halogen type and/or with Brönstedt sites by a method of isomerizing paraffinic hydrocarbons that consumes less catalyst in one or both reactors while maintaining the rate of isomerization of the effluents at a maximum.

The applicants have discovered and established that once every precaution has been taken to distribute the flow of fluids uniformly over the cross-section of the reactor or reactors, any sites destroyed by simple traces of water entrained by the reactants are not, in contrast to sites more or less deactivated by poisons from the isomerizing reaction, distributed simultaneously throughout the catalyst but are situated only in the upstream portion of the catalytic bed.

The applicants have accordingly discovered a surprising correlation between the rate of isomerization of the effluents and the number of sites destroyed in the upstream section of the isomerization reactor. It is accordingly possible to obtain information as to the state of the entire catalyst bed and to optimize utilization of the catalyst by replacing some of the used upstream catalyst once the rate of isomerization in the effluents begins to decrease without stopping the reactor in order to carry out time-consuming and expensive probes and without waiting for the catalyst to become totally exhausted from destruction of the sites.

When the equipment allows, it is also desirable to reverse the flow of the fluids through the reactor from time to time.

One preferred embodiment of the invention is, accordingly, a method of isomerizing n-paraffins into isoparaffins in a hydrocarbon cut essentially comprising either hydrocarbons with four carbon atoms or hydrocarbons with five and/or six carbon atoms, defined as follows. The cut being processed enters at least one reactor accommodating a stationary bed of catalyst, which it travels over. The catalyst comprises a support in the form of a refractory-metal oxide, 0.1 to 0.25% by weight of a platinum metal, and 2 to 10% by weight of chlorine. Isomerization occurs at a temperature of approximately 100° to approximately 200° C., in an atmosphere of approximately 7 to 60 bars, and at a rate of 0.5 to 12 volumes of charge per volume of catalyst per hour.

Either the rate of isomerization of the effluents or a parameter directly related thereto is preferably continuously measured. Some of the upstream catalyst, specifically between ⅓ and ⅔, is replaced with fresh catalyst once that rate has decreased between about 10 and about 30% below a predetermined value. The predetermined value being a set value which is the value of the parameter measured before any significant deactivation of the catalyst. Finally, the charge is redirected through the reactor once the catalyst has been replaced.

In practice, either the rate of isomerization of the effluents from the reactor or the octane number is measured continuously. If the charge is a $C_4$ cut, the isomerization rate is measured directly by chromatography. On the other hand, if the charge is a $C_5$–$C_6$ cut, the effluents' octane number is measured.

Flow of the charge is reversed in one preferred embodiment of the present invention once the catalyst has been replaced. Although the flow can always be reversed once the catalyst has been replaced, it is usually reversed periodically but not specifically after every replacement.

The present invention is based on the existence of a fairly precise correlation between a decrease in the rate of isomerization at the exit from the reactor and the amount of used upstream catalyst inside, as represented in the following Table 1.

TABLE 1

| Decrease in isomerization rate, in % | Upstream portion of catalyst to be replaced, in % |
|---|---|
| 10 | 33 |
| 15–20 | 50 |
| 30 | 66–75 |

Thus, it becomes possible to determine when it is necessary to replace some of the reactor's upstream catalyst (preferably ⅓ to ⅔ of all the catalyst in the reactor) from a decrease of 10 to 30% in the rate of isomerization of the reactor. This determination is possible without probing the catalyst bed as described in the present applicants' assignee's French Patent FR-A 2 566 530, hereby incorporated herein by reference.

Active catalyst sites are deactivated along an advancing front. This phenomenon is all the more evident in that the reactor includes, at the point where the charge is injected, means of diffusing the reactants as uniformly as possible throughout the reaction section and in that the reactor has been charged as homogeneously as possible by pouring out the catalyst in a fine and homogeneous flux falling like rain throughout the reactor's cross-section ("dense" charging), as described for example in U.S. Pat. No. 5,264,115 and French counterpart Patent FR-A 2 625 509, hereby incorporated herein by reference. Since the catalyst bed is homogeneous, the fluids will flow homogeneously throughout the reaction section, and the deactivation front deriving from the destruction of active sites will constitute a plane perpendicular to the flow and will advance downstream more or less regularly during the reaction.

While the portion of catalyst is being removed, it is possible to determine even more precisely the thickness of the catalyst bed being replaced by scanning across the bed to determine how far deactivation of the catalyst has progressed in the direction the charge is advancing. For instance, the level of chlorine in samples of catalyst obtained at various distances from the upstream face of the catalyst can be detected. This technique is possible because of the discovery of an abrupt increase in the level of chlorine immediately downstream of the catalyst-deactivation front. The thickness can accordingly be determined commencing at the upstream surface where the catalyst's chlorine content begins to decrease below a prescribed value, 5% for example.

The catalyst being replaced can be removed from the reactor by any means known in the art, by allowing it to flow subject to gravity for example out of a reactor that operates with the charge ascending or by pumping it up to the top of the reactor that operates with a descending charge. The reactor is then recharged from the top with fresh catalyst. The catalyst is introduced dense into an inert atmosphere, an atmosphere of anhydrous nitrogen for instance, by any conventional method.

As previously indicated, the isomerization of a $C_4$ or $C_5$–$C_6$ cut can then resume, with the charge's flow optionally reversed, and one will verify that the effluent isomerization rate of the isomerization unit remains approximately constant.

The method in accordance with the present invention can be carried out in a single reactor. This is particularly true of $C_4$ cuts, in which event a reactor of the type described in U.S. Pat. No. 4,985,209 and French counterpart Patent FR-A 2 623 732, hereby incorporated herein by reference, will preferably be employed because of the problems encountered when charging the reactor from the top and optionally reversing the charge's flow after replacing part of the catalyst.

A single reactor can also be employed for isomerizing charges of $C_5$–$C_6$, although it is generally preferable to employ two reactors for that process.

When two reactors are employed, the isomerization rate of the effluents from the downstream reactor is measured. The flow of catalyst through the upstream reactor is discontinued once that rate has decreased 10 to 30% below a prescribed level. A prescribed portion of the catalyst at the upstream end of the reactor is replaced with fresh catalyst. Flow of the charge resumes but is periodically reversed subsequent to one phase of catalyst replacement.

Isomerization continues without interruption in the other reactor while the first is out of operation. Once the prescribed portion of upstream catalyst in the first reactor has been replaced with fresh catalyst, isomerization begins again, with the flow of the charge being processed optionally reversed by procedures that are in themselves known. The upstream reactor now becomes the downstream reactor and vice versa.

BRIEF DESCRIPTION OF THE DRAWINGS

In this specification and in the accompanying drawings, we have shown and described preferred embodiments of our invention and have suggested various alternatives and modifications thereof; but it is to be understood that these are not intended to be exhaustive and that many other changes and modifications can be made within the scope of the invention. The suggestions herein are selected and included for purposes of illustration in order that others skilled in the art will more fully understand the invention and the principles thereof and will thus be enabled to modify it in a variety of forms, each as may be best suited to the conditions of a particular use.

FIG. 4 is a graph illustrating the activity of the effluents in terms of octane number as a function of time (measured in the downstream reactor);

FIG. 5 is a graph illustrating the decrease in the octane number of the effluents as a function of the deactivated portion of catalyst;

FIG. 6 is a graph illustrating that the catalyst deactivation front manifests itself as an abrupt increase in chlorine level.

DETAILED DESCRIPTION OF THE INVENTION

Figure 1:
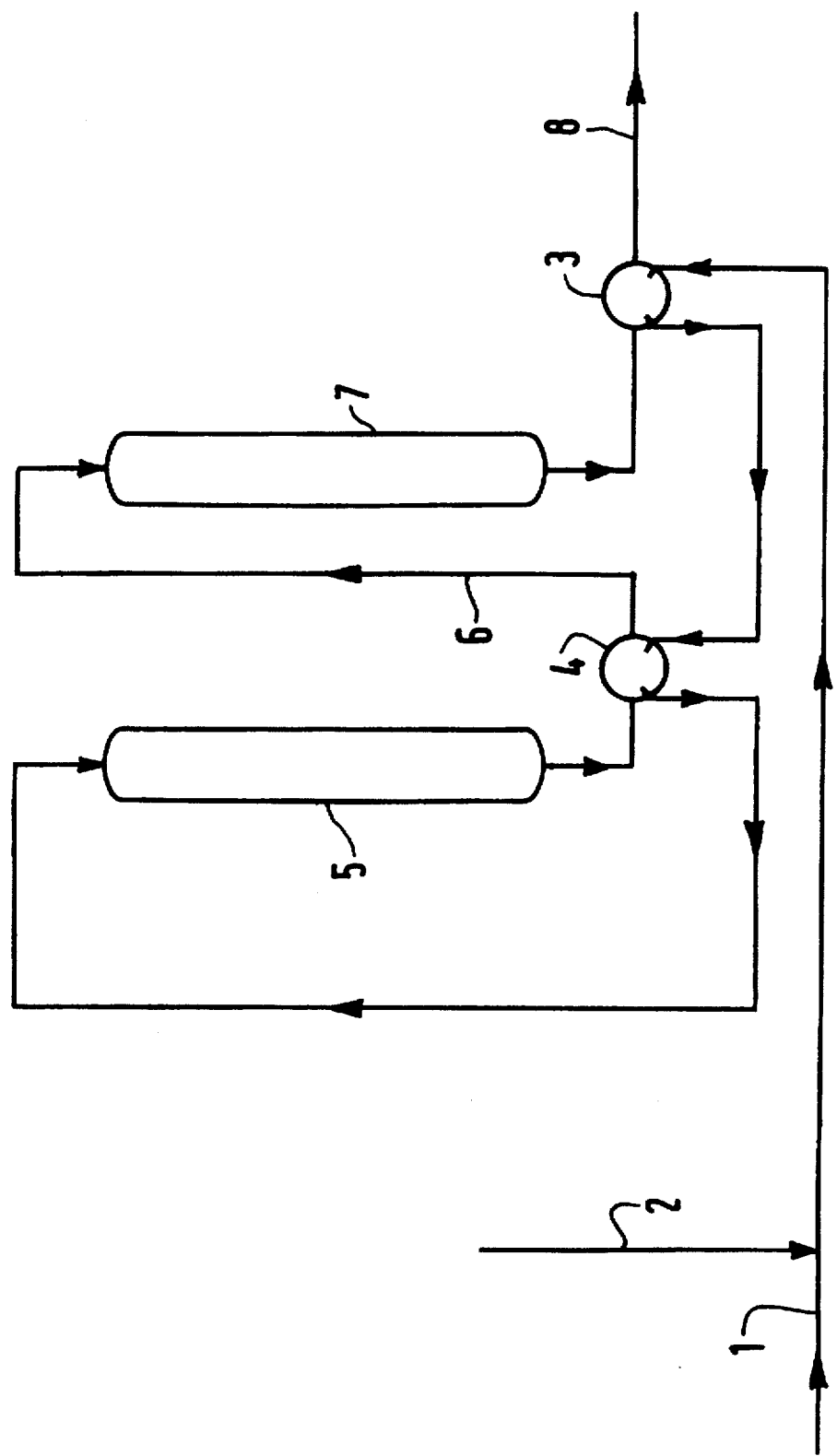
FIG. 1 is a schematic diagram illustrating the principle behind a plant comprising two reactors for isomerizing a $C_5$–$C_6$ cut of n-paraffins into isoparaffins.

The plant illustrated in FIG. 1 is of the classic design for isomerizing $C_5$–$C_6$ cuts of n-paraffins with two reactors, a first reactor 5 and a second reactor 7. The cut derives from an input line 1. Hydrogen and, optionally, recirculated gas are injected into the input line 1 from a gas line 2 to form a charge. The charge travels through a series of two heat exchangers, a first heat exchanger 3 and a second heat exchanger 4 in a direction opposite that of the effluents from the first reactor 5 and the second reactor 7. The charge is now introduced into the first reactor 5, the upstream reactor, which contains an isomerization catalyst. The effluent from the reactor 5 travels through the second heat exchanger 4 and, by way of a transfer line 6, into the second reactor 7, the downstream reactor, which also contains such a catalyst. Although the charge being processed in the illustrated plant happens to flow down through each reactor, it could just as well flow up. The second reactor 7 contains a charge that is high in isoparaffins and is evacuated by way of a outlet line 8. The effluent flows through first heat exchanger 3 and toward an unillustrated product-separator stage.

The plant includes unillustrated stopcocks that allow independent interruption and/or reversal of the flow to the first reactor 5 and the second reactor 7, respectively.

The plant also, of course, includes unillustrated instruments for measuring the octane number of the charge being processed and of the effluents from the first reactor 5 and the second reactor 7.

Since, as previously noted, "amorphous" catalysts are expensive and their Lewis and Brönstedt sites cannot be regenerated once they have been destroyed by water, all of the catalyst is usually removed from the upstream first reactor 5 before an equal amount of fresh catalyst is added. The flow of the charge being processed is then reversed, and the charge will enter the second reactor 7 first until the catalyst it contains is entirely exhausted. Every time a catalyst is removed from operation to remove the used catalyst and replace it with fresh or regenerated catalyst, the charge will flow only through the other reactor.

Figure 2:
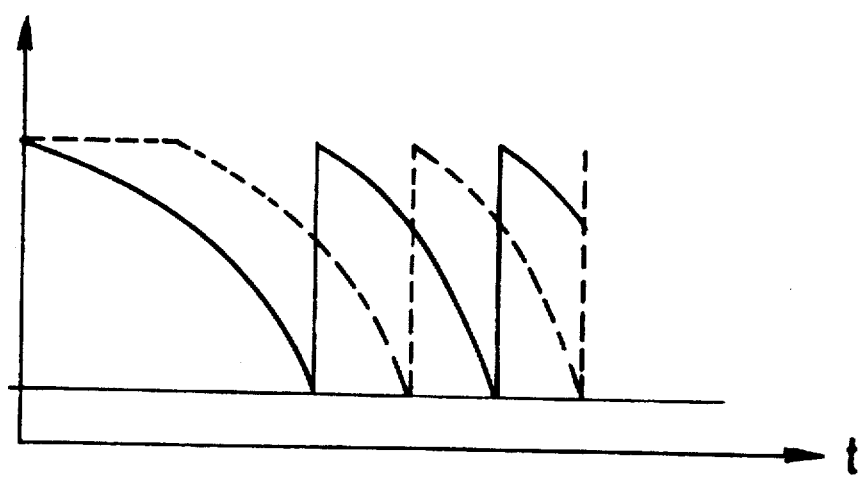
FIG. 2 is a graph of variations in the octane number of effluents from the plant, shown in FIG. 1, over time when all the catalyst is removed from the upstream reactor before fresh catalyst is added.

If the octane number of the charge being processed is measured as a function of time t both at the exit of the initially upstream reactor as represented by the dashed curve $R_1$, and at the exit of the initially downstream reactor as represented by the solid curve $R_2$ in FIG. 2, the results will begin to decrease at the exit of the downstream reactor long before the catalyst in the upstream reactor is replaced. This means that the catalyst in the reactor currently functioning as the downstream reactor begins to deactivate throughout the procedure long before the catalyst in the upstream has been replaced.

The octane number of the processed charge leaving the plant (the effluent from the downstream reactor) accordingly exhibits a series of maxima and minima represented by the peaks in the curves illustrated in FIG. 2. This means that the effluents' octane number does not remain at its maximum, that the charge has not been satisfactorily exploited, and that the procedure's economics can be improved.

It is precisely these drawbacks that the method in accordance with the present invention is intended to eliminate. All of the upstream catalyst is accordingly not removed from the upstream reactor, and only the upstream portion of the used catalyst is replaced when the octane number of the processed charge at the exit from the reactor decreases below a given point.

Figure 3:
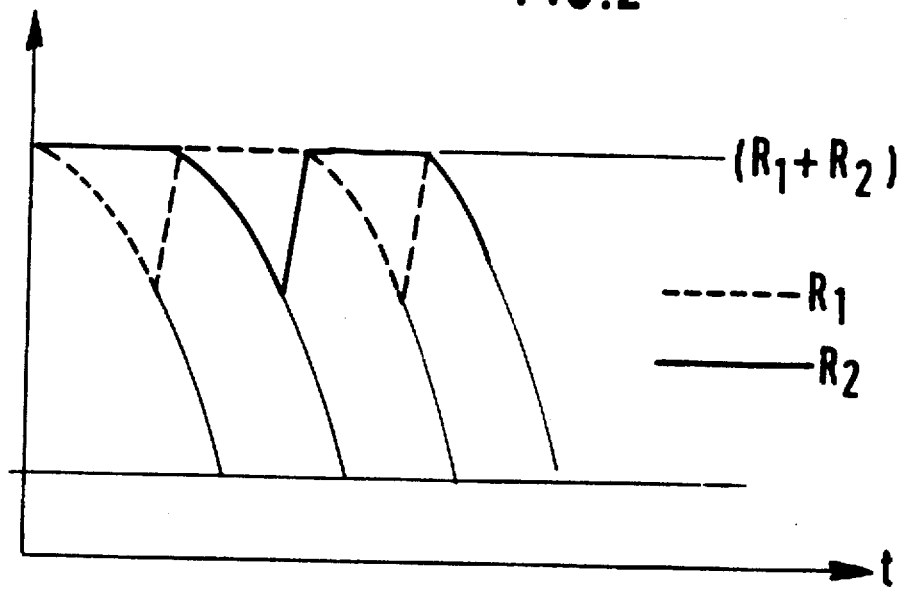
FIG. 3 is a graph similar to that in FIG. 2 but illustrating the relatively slight variations that occur in the octane number of effluents from the plant shown in FIG. 1 when the method in accordance with the present invention is employed.

As will be evident from FIG. 3, it is possible in accordance with the present invention to replace a used portion of the catalyst in the upstream reactor before the catalyst in the downstream reactor begins to deactivate or deactivate perceptibly. The octane number of the processed charge will accordingly remain almost constantly at its maximum, which is a considerable advantage over the conventional method.

Figure 7:
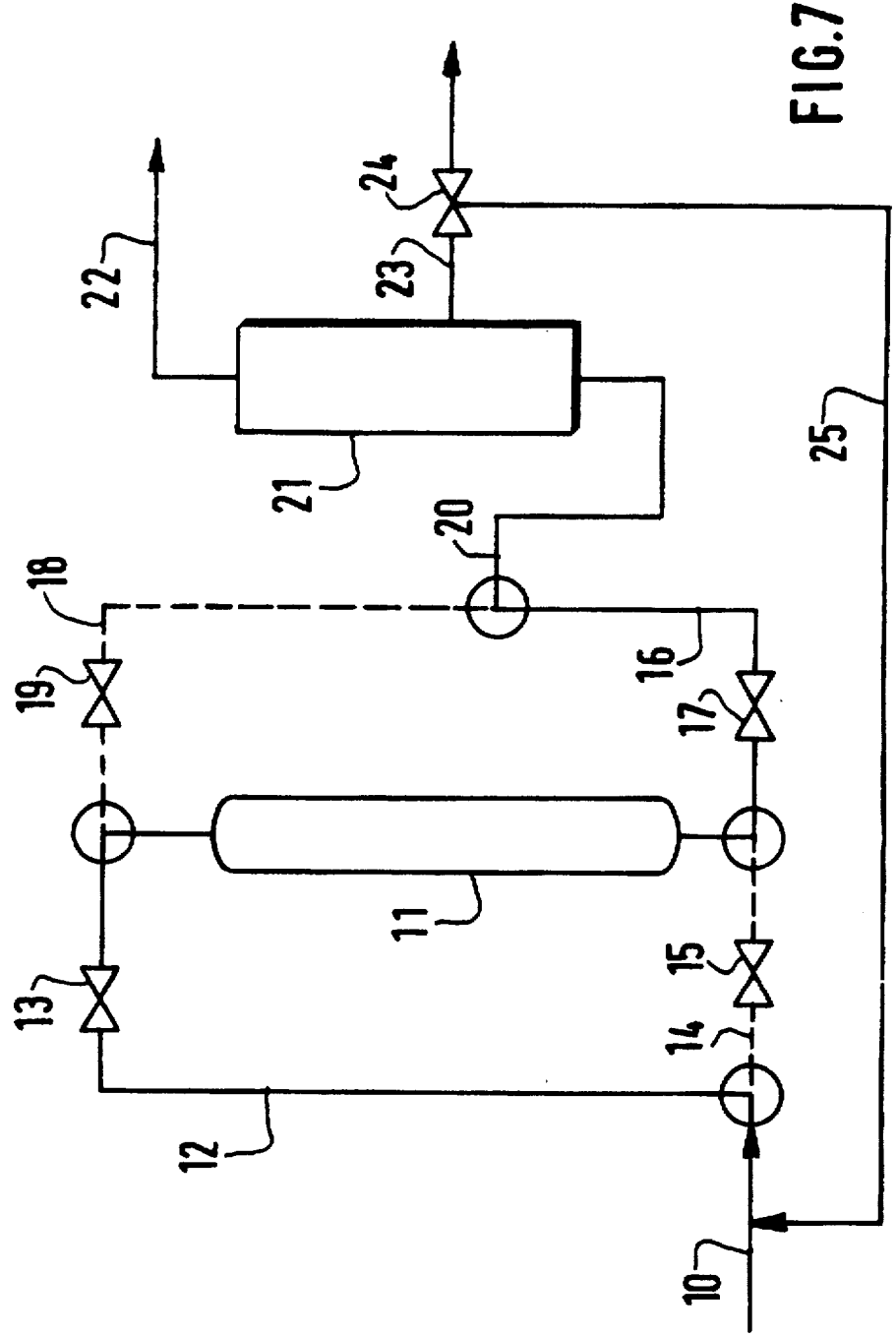
FIG. 7 is a schematic diagram illustrating how the method in accordance with the present invention can be employed with a single reactor to isomerize a $C_4$ cut for example.

FIG. 7 illustrates how the present invention can be employed with a single isomerization reactor. In this event, as previously indicated, it is practical to employ a reactor of the type described in U.S. Pat. No. 4,985,209 and counterpart French Patent FR-A 2 623 732.

The charge to be processed arrives by way of a charge line 10 and can be introduced either at the top of a third reactor 11 by way of a first line 12 that accommodates a first stopcock 13 or at the bottom by way of a second line 14 provided with a second stopcock 15.

The processed charge is evacuated respectively either at the bottom of the third reactor 11 by way of a single line 16 that accommodates a third stopcock 17 or at the top by way of a fourth line 18 that accommodates a fourth stopcock 19. The effluents are now conveyed by way of a feed line 20 to the bottom of a separation column 21, from which they are evacuated at the top by way of an effluent line 22, while the residual n-paraffins are evacuated from half-way up by way of a residual line 23 that accommodates a fifth stopcock 24. The n-paraffins are ultimately recirculated by way of a recirculation line 25 which injects these n-paraffins into the charge line 10 supplying the single reactor 11.

The following example is intended without limiting the scope of the invention in any way to illustrate how the method in accordance with the present invention can be applied to isomerizing a $C_5$–$C_6$ cut in a series of two reactors. The charge is a $C_5$–$C_6$ cut with the following composition by percent by weight:

| | | |
|---|---|---|
| i-$C_4$: | 0.00 | |
| n-$C_4$: | 0.36 | |
| i-$C_5$: | 20.05 | |
| n-$C_5$: | 38.50 | |
| 2-2-dimeth-$C_4$: | 1.40 | |
| 2-3-dimeth-$C_4$: | 2.28 | |
| 2-meth-$C_5$: | 2.80 | |
| 3-meth-$C_5$: | 11.89 | |
| n-$C_6$: | 7.32 | |
| cyclo-$C_5$: | 11.81 | |
| methyl cyclo-$C_5$: | 1.28 | naphthene |
| cyclo-$C_6$: | 0.16 | reaction inhibitors |
| benzene: | 0.78 | (totaling 2.22%) |
| $C_7^+$: | 1.37 | |

The plant is of the type illustrated in FIG. 1, including a series of two reactors. The unreacted effluents from the downstream (second) reactor are recirculated at the bottom of a separation column.

Each reactor contains 25 metric tons of a catalyst prepared as described in U.S. Pat. No. 5,151,400 and counterpart European Patent No. 409 679, hereby incorporated herein by reference. This material is a monofunctional Friedel-Crafts acid catalyst on a support of aluminum treated with aluminum chloride or other aluminum-organic derivative to produce

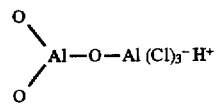

sites.

The operation will now be specified:
2000 tons of fresh charge are processed per day (2.8 volumes of charge per volume of catalyst per hour).
400 tons of unreacted effluents are obtained from the base of the effluent-distillation column and recirculated.
The total isomerization rate,

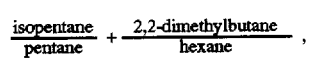

is determined by chromatography of the charge and effluents.

The octane number of the effluents from the two reactors is also measured.

As measured at the exit from the first reactor, the total isomerization rate is 94 and the octane number 80. The total isomerization rate at the exit from the second reactor is 112.

The total isomerization rate of the isomer subsequent to separation of the effluents from the second reactor is 135 and the octane number 87.5.

Figure 5:
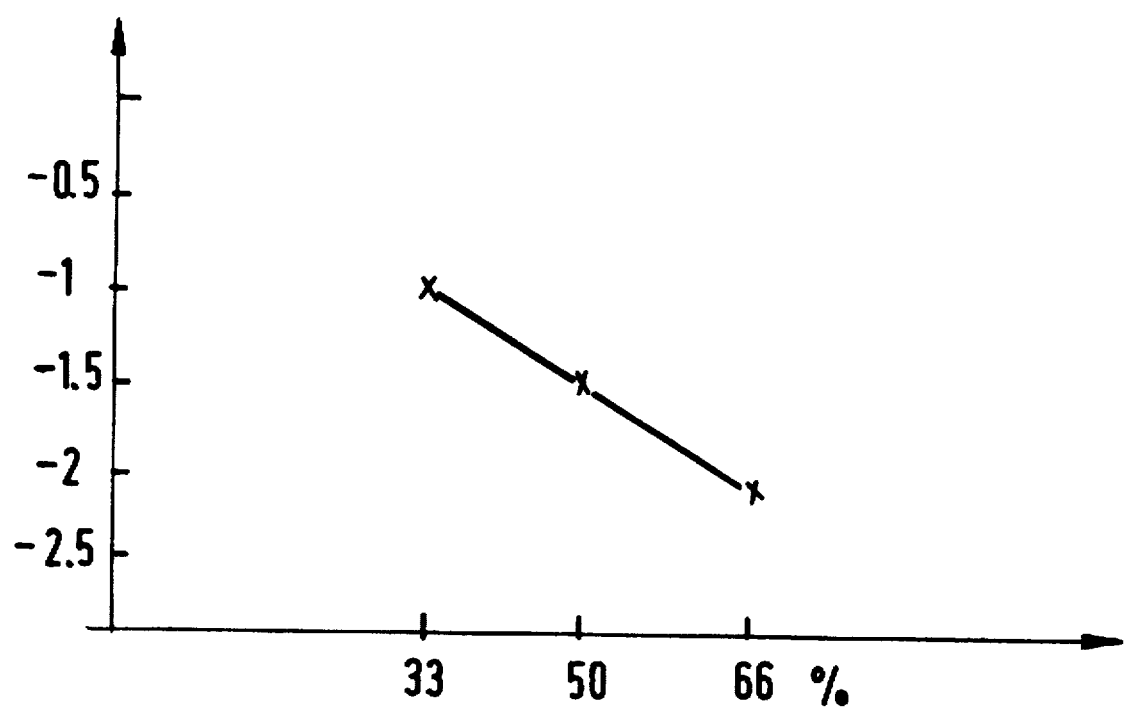

FIG. 5 illustrates the decrease in the octane number of the effluents from the first reactor as a function of the deactivated portion in percent by weight. The excellent, practically linear, correlation between the decrease in the effluents' octane number and the portion of deactivated catalyst will be evident. The octane number decreases 10 to 25% as the portion of deactivated catalyst increases from 33 to 66%.

It is accordingly possible, by measuring the octane number of the effluents from either the first or the second reactor in the direction traveled by the charge being isomerized, to determine both the best moment to stop that reactor and how much of the upstream catalyst within that reactor to replace.

Figure 6:
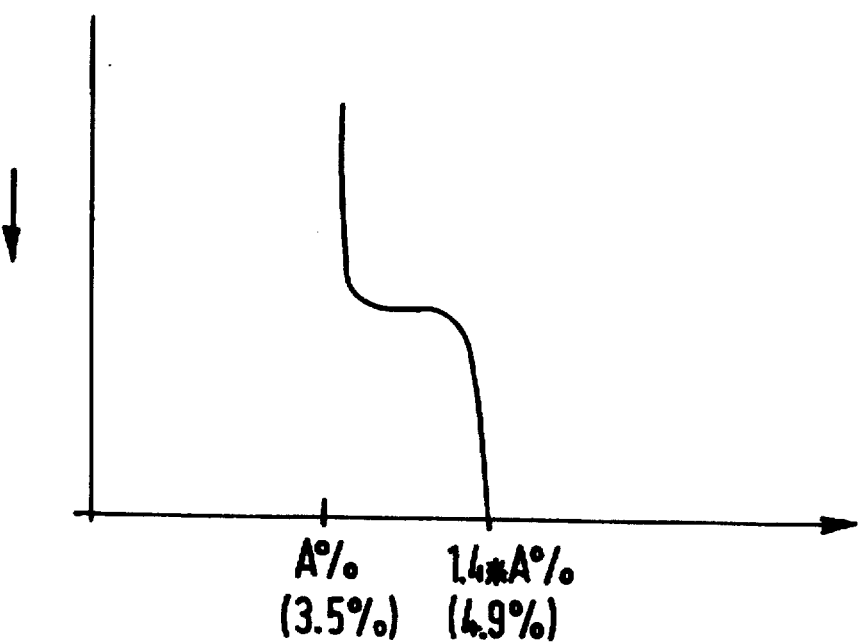

If the chlorine content in the same reactor with the charge flowing downward is measured with a probe as a function of distance from the upstream face of the catalyst, it will be evident from FIG. 6 that the catalyst-deactivation front manifests itself as an abrupt increase in the chlorine content, which translates into a horizontal section of the curve.

Figure 4:
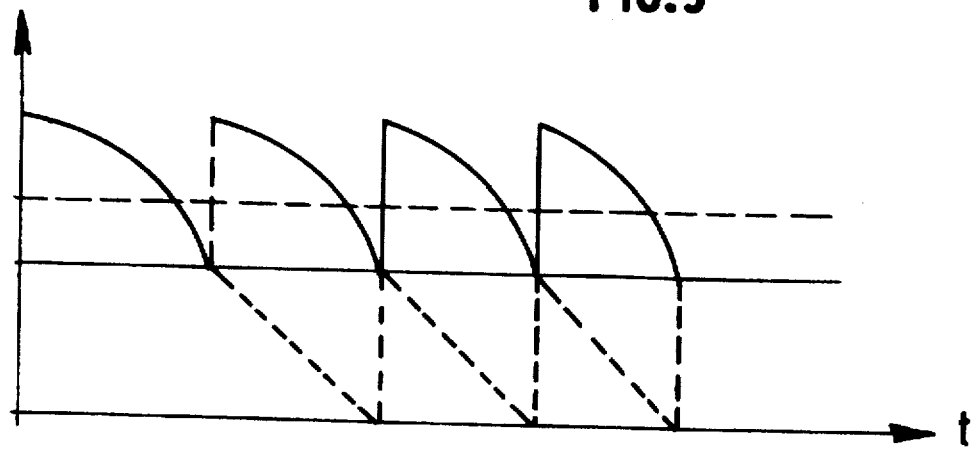
FIGS. 4, 5, and 6 are graphs illustrating tests conducted on the preferred embodiments specified hereinafter with reference to the examples.

FIG. 4 illustrates the activity of the effluents of the downstream reactor as a function of time. It reveals how the present invention considerably increases the octane number of the effluents from 78.5 to 79.3, a difference of 0.8.

The present invention is accordingly a simple and easy method of maintaining a high octane number in the products from the isomerization of a $C_4$ or $C_5$–$C_6$ cut.

What is claimed is:

1. A method of isomerizing into isoparaffins a charge of n-paraffins comprising either hydrocarbons with four carbon atoms or hydrocarbons with five and/or six carbon atoms, said method comprising the steps of:
   a) passing a continuous charge through at least one reactor which contains a stationary bed of catalyst, wherein said catalyst comprises a support in the form of a refractory-metal oxide with 0.1 to 0.25% by weight of a platinum metal and 2 to 10% by weight of chlorine;
   b) isomerizing said charge in said reactor(s) at a temperature of approximately 100° to 200° C., in an atmosphere of approximately 7 to 60 bars, and at a rate of 0.5 to 12 volumes of charge per volume of catalyst per hour;

c) continuously determining at least at appropriate intervals the rate of isomerization by measuring directly the isomeric content in the effluents or by measuring the extent in the effluents of a parameter whose presence is dependent on the degree of isomerization in the effluents, including obtaining the originally determined isomeric value;

d) discontinuing flow of the charge through the most upstream reactor and replacing between approximately ⅓ and ⅔ of the upstream catalyst therein with fresh catalyst once the rate of isomerization of the processed charge or the parameter directly dependent on the rate of isomerization has decreased 10 to 30% to below the originally determined value; and e) redirecting the charge through the reactor once the catalyst has been replaced.

2. The method as claimed in claim 1, wherein the step of replacing the upstream catalyst comprises replacing approximately ⅓ of the upstream catalyst in the upstream reactor once the rate of isomerization in the effluents of the processed charge or the parameter directly related thereto has decreased approximately 10%.

3. The method as claimed in claim 1, wherein the step of replacing the upstream catalyst comprises replacing approximately ½ the upstream catalyst in the upstream reactor once the rate of isomerization in the effluents from the processed charge or the parameter directly related thereto has decreased between approximately 15 to 20%.

4. The method as claimed in claim 1, wherein the step of replacing the upstream catalyst comprises replacing approximately the upstream 60 to 75% of the catalyst in the upstream reactor once the rate of isomerization in the effluents of the processed charge or the parameter directly related thereto has decreased approximately 30%.

5. The method as claimed in claim 1, wherein the step of continuously measuring the rate of isomerization in the effluents from the reactor is accomplished by chromatography of the charge and of the effluents.

6. The method as claimed in claim 1, wherein the step of continuously measuring the rate of isomerization in the effluents from the reactor comprises measuring the octane number of the charge and of the effluents.

7. The method as claimed in one of claims 1 through 6, wherein the upstream portion of the catalyst to be replaced with fresh catalyst is determined by probing the catalyst commencing at its upstream end.

8. The method as claimed in claim 7, wherein the catalyst inside the reactor is probed to determine the chlorine content in the catalyst.

9. The method as claimed in claim 8, wherein the portion of the catalyst in the reactor replaced is upstream of that section of the bed of catalyst where the level of chlorine content in the catalyst varies most abruptly when moving between the upstream and downstream portions of the bed.

10. The method as claimed in claim 9, wherein variation in the level of chloride content is on the order of 5% from the chlorine content level in the upstream section of the bed.

11. The method as claimed in claim 1, wherein only one isomerization reactor is employed.

12. The method as claimed in claim 9, wherein only one isomerization reactor is employed.

13. The method as claimed in claim 1, characterized in that the reactor or reactors are charged by homogenous dense charging.

14. The method as claimed in claim 9, in that the reactor or reactors are charged by homogenous dense charging.

15. The method as claimed in claim 1, wherein a series of two isomerization reactors are employed, the isomerization rate of the effluents from the downstream reactor or a parameter directly related thereto is measured, the flow of catalyst through the upstream reactor is discontinued once that rate or parameter has decreased 10 to 30% below a set value, a prescribed portion of the catalyst at the upstream end of the reactor is replaced with fresh catalyst, and flow of the charge resumes but is periodically reversed subsequent to one phase of catalyst replacement.

16. The method as claimed in claim 9, wherein a series of two isomerization reactors are employed, the isomerization rate of the effluents from the downstream reactor or a parameter directly related thereto is measured, the flow of catalyst through the upstream reactor is discontinued once that rate or parameter has decreased 10 to 30% below a prescribed level, a prescribed portion of the catalyst at the upstream end of the reactor is replaced with fresh catalyst, and flow of the charge resumes but is periodically reversed subsequent to one phase of catalyst replacement.

17. The method as claimed in claim 1, wherein said set value is the value of the parameter measured before any significant deactivation of the catalyst.

18. The method as claimed in claim 9, wherein said set value is the value of the parameter measured before any significant deactivation of the catalyst.

19. The method as claimed in claim 15, wherein said set value is the value of the parameter measured before any significant deactivation of the catalyst.

20. The method as claimed in claim 16, wherein said set value is the value of the parameter measured before any significant deactivation of the catalyst.

* * * * *